United States Patent [19]

Bickar

[11] Patent Number: 5,496,737

[45] Date of Patent: Mar. 5, 1996

[54] SOLVENTLESS PROTEIN ASSAY STANDARD

[76] Inventor: David Bickar, 27 Stonepath La., Easthampton, Mass. 01027

[21] Appl. No.: 137,501

[22] Filed: Oct. 15, 1993

Related U.S. Application Data

[63] Continuation-in-part of Ser. No. 804,964, Dec. 11, 1991, abandoned.

[51] Int. Cl.$^6$ .................................................. G01N 33/00
[52] U.S. Cl. ................... 436/86; 436/8; 436/15; 436/87; 436/88
[58] Field of Search .................. 436/8, 15, 18, 436/86, 87, 88

[56] References Cited

U.S. PATENT DOCUMENTS

| | | | |
|---|---|---|---|
| 4,023,933 | 5/1977 | Bradford et al. | 23/230 B |
| 4,219,337 | 8/1980 | Grossberg et al. | 23/230 B |
| 4,337,064 | 6/1982 | Gindler | 23/230 B |
| 4,507,233 | 3/1985 | Saito et al. | 260/115 |
| 5,077,222 | 12/1991 | Lau | 436/88 |

*Primary Examiner*—Donald E. Czaja
*Assistant Examiner*—Lien Tran
*Attorney, Agent, or Firm*—Paul G. Lunn

[57] ABSTRACT

A method for preparing a solventless protein standard is disclosed in which a solventless dye indicator and a predetermined amount of solventless protein are placed in an appropriate receptacle such as the well of a multiwell plate. This results in a solventless protein standard in which the solventless protein and the solventless dye are contained within the same receptacle. When an appropriate solvent is added to the receptacle, the protein and dye react together to produce a color change which is detectable, and which can be used as a standard for a protein assay using that dye. Also claimed is the solventless protein assay standard produced by the process.

11 Claims, 3 Drawing Sheets ns5,496,737

SOLVENTLESS PROTEIN ASSAY STANDARD

The present application is a continuation-in-part of U.S. application Ser. No. 07/804,964 filed Dec. 11, 1991, now abandoned.

FIELD OF THE INVENTION

The present invention lies in the field of protein chemistry.

BACKGROUND OF THE INVENTION

The determination of the total protein present within a solution is important in many analytical procedures, such as in the determination of the purity of a protein and in determining the protein chemistry of a blood or urine sample.

Four spectroscopic methods are routinely used to determine the concentration of protein in a solution. These include measurement of the protein's intrinsic ultraviolet (U.V.) absorbance, and three methods which generate a protein-dependent color change, namely, the Lowry assay, the Smith copper/bicinchoninic assay and the Bradford dye assay. Although one or more of these methods is used routinely in almost every biochemical laboratory, none of the procedures are particularly convenient for the reasons described below.

The first, U.V. absorbance, has limited application since for accuracy it requires a pure protein with known extinction coefficient in a solution free of interfering substances. The Lowry and copper/bicinchoninic assays require the preparation of several reagent solutions, which must be carefully measured and mixed during the assay. This is followed by lengthy, precisely timed incubations at closely controlled, elevated temperatures, and then immediate absorbance measurements of the unstable solutions. Both assays may be affected by other substances frequently present in biochemical solutions, including detergents, lipids, buffers and reducing agents. To control for these factors, every assay must also include a series of standards, each with a different, known concentration of added protein, but otherwise having the same composition as the sample solutions. The Bradford dye assay is faster, involves fewer mixing steps, does not require heating, and gives a more stable colorimetric response than the two previous assays. Like them, however, its response is quite prone to influence from nonprotein sources, and protein standard solutions are necessary.

The preparation of the protein standards is tedious and error-prone. Protein preparations, usually of bovine serum albumin, are available as preweighed powder or in sterile solutions of measured concentration, but their use in preparing standard solutions still requires several precise measurements and dilutions. Frequently this involves compromises between convenience, precision, and the requirement that the standards contain the same concentrations of nonprotein components as the sample solutions. For many applications, during protein purification, for example, the protein concentrations of several different solutions need to be assayed. Unless a set of protein standards is prepared for each of the different solutions, the assay results may be wrong. Further, protein standard solutions are inherently unstable, and decompose at varying rates depending on factors which include their composition, pH, sterility and conditions of storage. This reduces the reliability of the standard solutions, and hence of the assay itself, and requires the frequent preparation of new standard solutions.

In conclusion, protein assays are inconvenient and sometimes unreliable due to the problems associated with the preparation of the necessary protein standards. A method which allowed protein assays to be performed without these problems would be of considerable value. Thus, there is a need for a protein assay standard in which the preparation of standard solutions is eliminated.

SUMMARY OF THE INVENTION

The present invention fills this need by providing for a solventless, protein-assay standard comprised of a receptacle, said receptacle containing a solventless dye and a dehydrated protein wherein upon addition of an appropriate solvent, the dye and protein react together to produce a detectable color change indicating the presence and/or amount of protein.

The present invention further provides for a method for preparing a solventless protein standard comprising:

preparing a dye solution containing a dye and a dye solvent;

placing an aliquot of the dye solution within a receptacle;

removing the dye solvent; preparing a protein solution containing a protein and protein solvent;

placing an aliquot of the protein solution within the receptacle containing the dye; and removing the protein solvent such that the receptacle contains a solventless dye and a solventless protein.

A protectant or stabilizer such as anhydrous glycerol can be added to the solventless mixture. Generally, the protectant is placed between the dye and the protein.

Alternatively, the order can be reversed such that the aliquot of the protein solution can be placed into the receptacle first; the solvent removed and then the dye solution can be placed into the receptacle and the solvent removed.

DETAILED DESCRIPTION OF THE INVENTION

Figure 1:
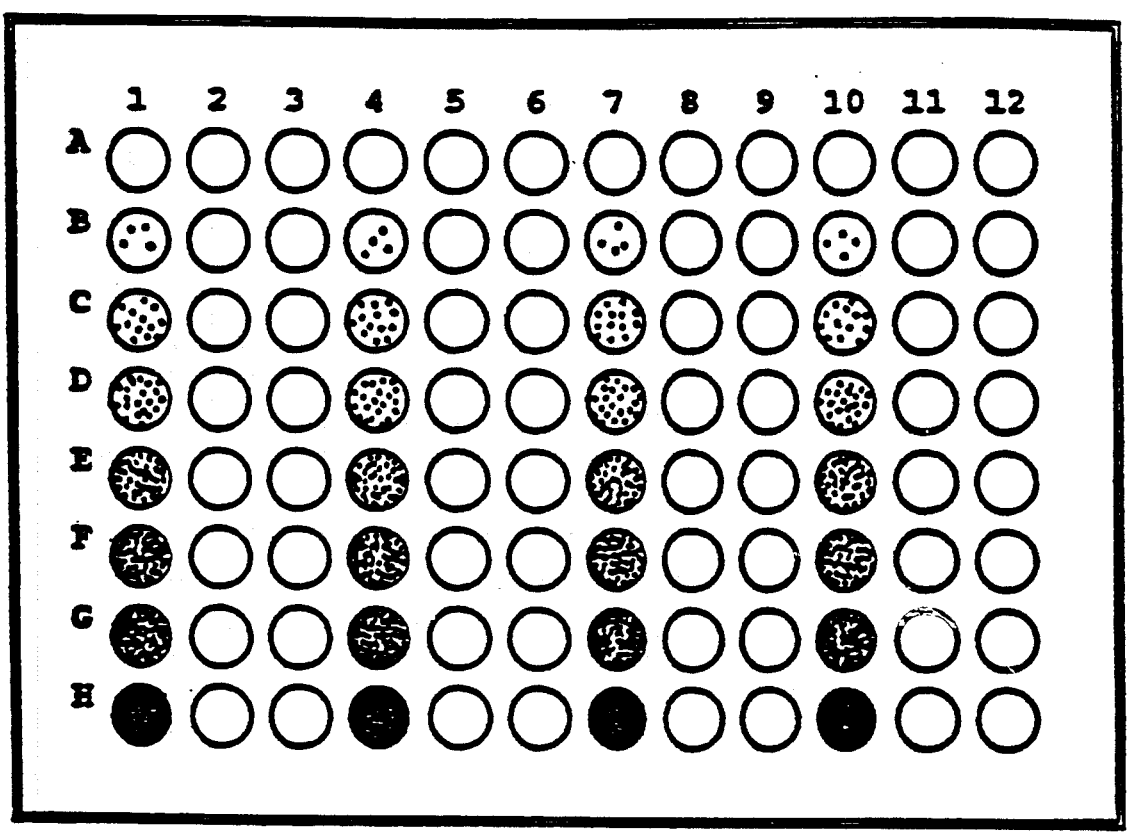
FIG. 1 represents a multiwell plate like that used in Example 1. Each well initially contained the solventless dye, and the wells in columns 1,4,7 and 10 also contained the anhydrous protein standards. The wells were treated with 250 µl of water to produce a protein concentration-dependent color change.
Figure 2:
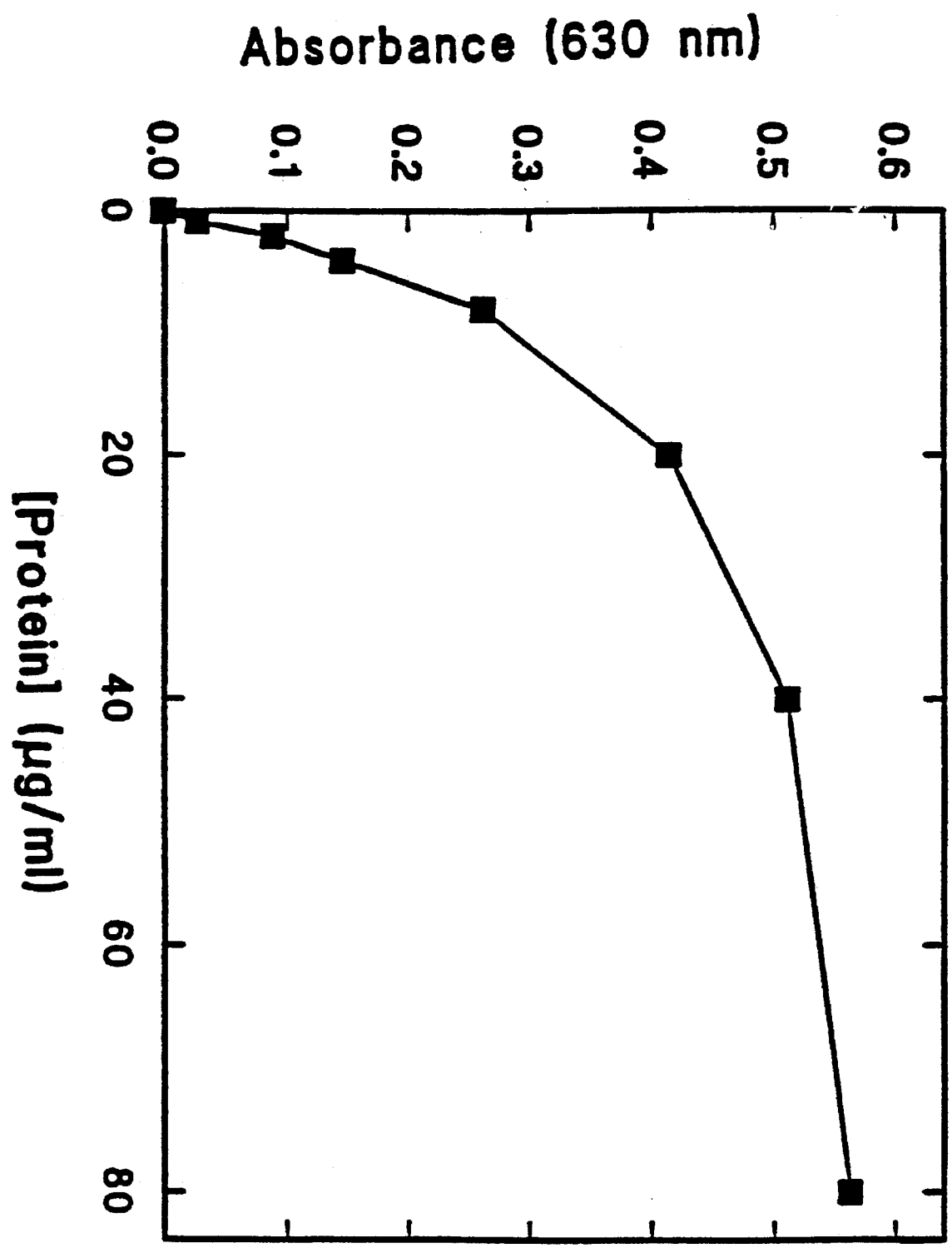
FIG. 2 shows a graph of Absorbance (630 nm) vs [Protein] (µg/ml) for a multiwell plate with solventless dye and anhydrous protein standards prepared as described in Example 1. Anhydrous bovine serum albumin (BSA) and solventless dye were dissolved in 250 µl of distilled water per well and their absorbance at 630 nm determined.
Figure 3:
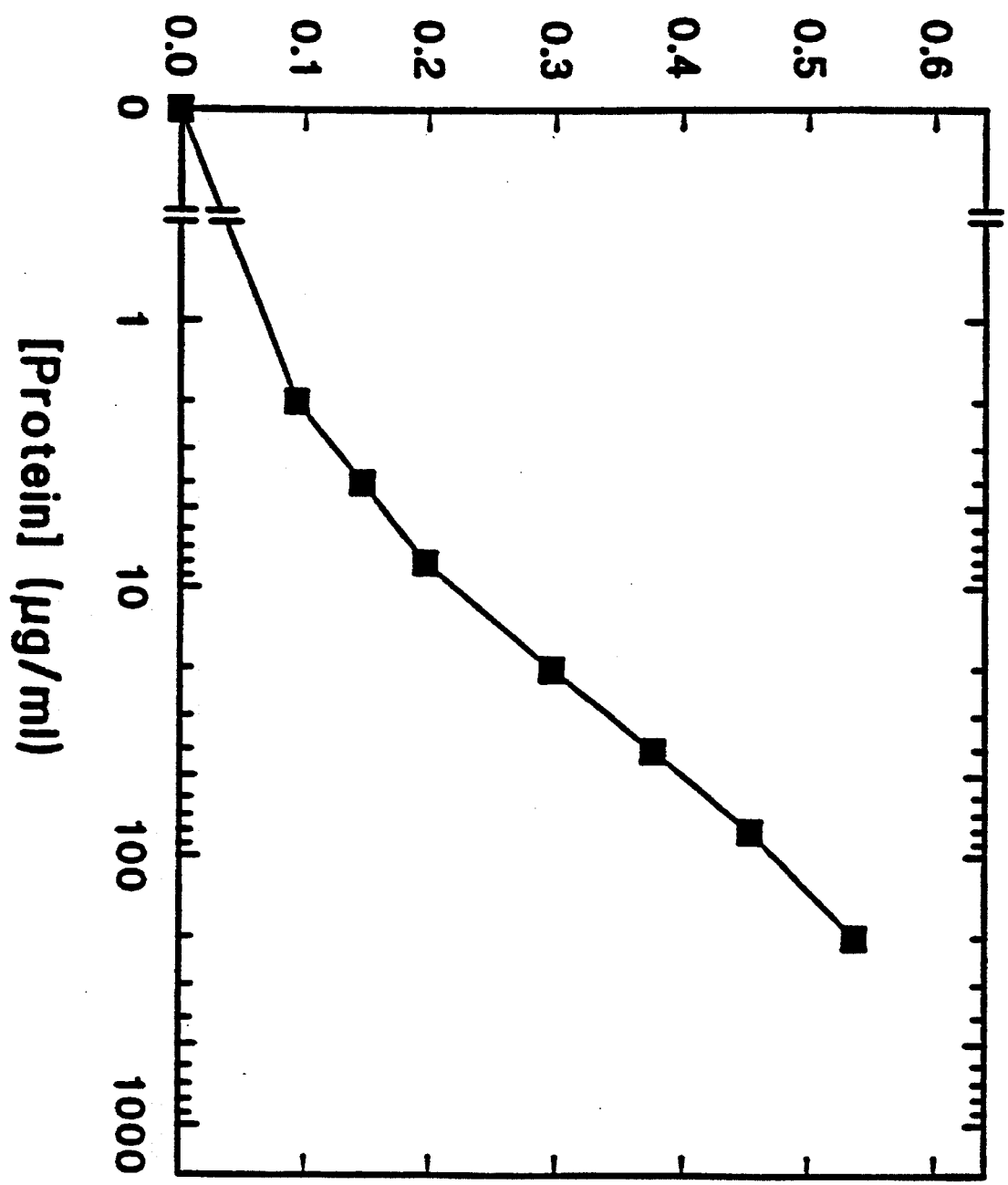
FIG. 3 shows a graph of Absorbance (630 nm) vs Log [Protein] (µg/ml) for a second multiwell plate with solventless dye and anhydrous protein standards, prepared as described in Example 1. However, the second plate was stored at room temperature for 30 days before the dye and protein (BSA) were dissolved in 200 µl of distilled water per well (instead of 250 µl/well as in the plate of FIG. 2) and their absorbance at 630 nm determined. The absorbance is plotted against the log of the protein concentration.

Accordingly, the present invention is comprised of a receptacle, said receptacle containing a solventless reagent and a dehydrated protein, wherein upon addition of an appropriate solvent the reagent and protein react together to produce a detectable color change indicating the presence and/or amount of protein.

The present invention is further comprised of a method for preparing a solventless protein standard in which a dye indicator and a predetermined amount of protein are included. An aliquot of the dye solution is placed into an appropriate receptacle such as the well of a multiwell plate and the solvent is removed from the indicator dye solution resulting in solventless dye being within the receptacle. An aliquot of the protein solution is then placed within the same receptacle as the dye and on top of the dye. The solvent is removed from the protein solution in a manner such that the protein is not hydrolyzed. This results in an solventless protein standard in which the standard solventless protein and the solventless dye are contained within the same receptacle such that when an appropriate solvent is added to the receptacle, the protein and dye will react together to produce a detectable color change.

The present invention is based upon the discovery that if a known amount of solvent is place into a receptacle containing a solventless protein-reactive reagent and a known amount of anhydrous protein, the intensity of the color change of the resultant protein-reagent solution will reflect the concentration or amount of protein present per unit volume. A series of solventless protein/reagent mixtures can then be made, so that for a series of receptacles, such as the wells of multiwell plate, each individual receptacle in the series has a different, known amount of protein. If the same amount of solvent is added to each receptacle, the intensity of the resultant color change in each of the receptacles will be proportional to the concentration of the protein present in the resultant solution.

Furthermore, in order to determine the concentration of protein in a solution, the solventless protein-reactive reagent can be placed into a receptacle, but without the addition of protein. A volume of the solution (corresponding to the volume of the solvent placed into the receptacles with the known protein/dye mixture above) containing an unknown amount of protein can be placed into the receptacle containing only the protein-reactive reagent. Any resultant color change of the unknown solution is then compared to the color changes of each of the solutions containing known amounts of protein. The concentration of protein in the unknown solution will approximate the protein concentration of the known solution whose color is closest to the color of the unknown solution.

More accurate estimations of protein concentration can be made by determining the changes in light absorbance spectroscopically for each of the receptacles in a series of protein/reagent mixtures. By plotting the change in light absorbance of the solutions against the concentration of protein contained in each of the receptacles in the series, a line can be made, showing the change in light absorbance for any concentration of protein below that of the highest in the series. By then measuring the change in light absorbance of a solution containing an unknown concentration of protein, the concentration of protein in the unknown solution can be determined from the graph, by finding the protein concentration at which the absorbance value for the line is equal to the absorbance of the solution.

According to the present invention "color change" or "change in light absorbance" is defined as any change in the frequency, intensity or spectral envelope of the light absorbance, emission or fluorescence that occurs due to the reaction of the protein-reactive reagent with a protein.

The individual steps of the process of the present invention are described in detail below.

I. Dye Solution Preparation

A. Selection of Dye

Any dye which upon binding or reacting with a protein can undergo a change in spectroscopic properties can be used for protein determination. Some of the important properties of a dye for predicting its usefulness in protein determination include its affinity for different proteins, reactions with interfering substances, stability, solubility, absorbance maximum and extinction coefficient.

B. Solvent Used with the Dye

The solvent used to dissolve the dye is dependent on the particular dye employed, and the final assay conditions required. In addition to aqueous and organic solvents and their mixtures, other useful solvents include organic and inorganic acids, such as acetic, phosphoric, polyphosphoric and sulfuric acids. Bases, such as pyridine and triethylamine may also be used.

C. Dye Solution Preparation

The dye solution is then prepared by techniques determined by the dye and solvent employed.

II. Placing the Dye on the Multiwell Plate

A. Dye Addition

A dye in solution, as well as other reagents necessary for the protein assay, can be easily and accurately added to the wells of a multiwell plate. Small volumes of solutions containing accurately measured amounts of the necessary reagents can be added to each well using standard laboratory equipment, including automated devices for multiple additions.

| Protein Stains | |
|---|---|
| Alcian Blue | |
| Acid Violet 17 | (C.I. 42650) |
| Amido Black 10B | (C.I. 20470) |
| Bromophenol Blue | |
| Benzopurpin 4B | |
| Coomassie brilliant blue R250 | (C.I. 42660) |
| Coomassie brilliant blue G250 | (C.I. 42655) |
| Copper phthalocyanine tetrasulfonic acid (CPTS) | (C.I. 74220) |
| Iron phthalocyanine tetrasulfonic acid | |
| Phthalocyanine tetrasulfonic acid | |
| Nickel phthalocyanine tetrasulfonic acid | |
| Sulforhodamine B | |
| Serva Blue W | (C.I. 42645) |
| Ponceau S | (C.I. 27195) |
| Fast Green FCF | (C.I. 42053) |
| Eosin Y | (C.I. 45380) |
| Reactive Blue 15 | (C.I. 61205) |
| Reactive Red 4 | (C.I. 18105) |
| Stains-All | (C.I. 62160) |
| Benzyl Violet | (C.I. 42640) |

B. Solvent Removal

Solvents can be removed by evaporation, aided by heating, reduced pressure, or by using a stream of gas or air. Care must be taken that the conditions used do not degrade or remove the dye or other reagents necessary for the assay.

III. Preparation of Protein Standards

A. Protein Used

The protein used to prepare the standards should give a response upon reaction with the chosen dye, sufficient to allow a determination of the concentration of protein in an unknown solution by comparing the dye response of the unknown solution with the dye response of the protein standard solution.

B. Solvent Used for Protein Standards

Protein standards should be prepared in solvents which provide sufficient solubility and protein stability to ensure reproducible applications. The solvent should also be easily removed, and not interfere with the subsequent assay. Detergents or buffer concentrations which interfere with the protein assay should be avoided.

IV. Placing the Protein on the Plate

A. The protein can be added to a multiwell plate using the same procedures described in Section IIA.

B. Solvent Removal

Solvents used to aid in addition of the protein to the multiwell plates can be removed by essentially the same procedures described in Section IIB, but care must be taken to ensure that the dye response is not decreased by protein hydrolysis during drying. If necessary, this can be prevented by removing the solvent by evaporation of the frozen solution (lyophilization), or by using nonaqueous solutions, or by incorporating a "protectant" layer between the protein solution and the assay components (see Section V).

V. Protectants

Protectants are any materials which decrease or prevent the mixing or reaction of the assay reagents with the protein standards during preparation of the solventless standards. These include compounds which increase the viscosity of the assay reagents or the solutions of protein standards, such as glycerol or glucose, or dehydrating agents such as polyphosphates, which combine with water before it can hydrolyze the proteins, or materials which can form a temporary barrier between the assay reagents and the protein solution during drying, such as glycerol or compounds sparingly soluble in the protein solution. Protectants must be thoroughly tested to ensure that they do not interfere with the actual protein assay.

VI. Use of Prepared Standards

The solventless combined protein standards and assay reagents in the wells of a multiwell plate should be dissolved by adding an appropriate solvent, similar to that of the solution to be assayed, but without protein. Upon addition of the solvent, a reaction occurs between the solventless protein and dye within the well. Furthermore, the protein concentration of a solution can be determined by applying the protein-containing solution to a neighboring well containing only the solventless assay dye. The unknown protein concentration of the solution can be then determined by comparing the dye response in each of the wells containing known concentrations of protein with the response in the well containing the solution of unknown protein concentration.

It is critically important that the same volume of solvent is added to each of the wells in order to obtain an accurate estimation of the protein concentration of the unknown solution.

Thorough mixing of the solventless components with the aqueous solutions can be achieved by inverting the (resealed) multiwell plate or by agitating the plate. Mixing by agitation is most conveniently performed by using a plate reader with this capacity, but a vortex mixer, shaker, or sonicator may also be used.

Normally, upon addition of solvent to a well containing the solventless reagents, the dye will react with any protein present in the solvent, and, in those wells used to determine the standard curve, with the previously anhydrous protein already present in the well. In some cases, however, the solvent may contain substances which interfere with the protein-dye reaction. If the interference is uniform, and small relative to the response from the protein-dye reactions of the protein standards, it can be measured and eliminated by subtracting it from the dye response of each sample. An example of this type of interference would be a small dye response due to traces of protein or detergents from the inadequately rinsed glassware. If the interference is large, however, it presents a more serious problem. For example, proteins or detergents are sometimes added to solutions to stabilize or protect a particular enzyme or protein of interest. In such cases, the added protein or detergent may cause such a large dye reaction that it is impossible to determine the concentration of the other proteins in the solution. If the dye reaction is due to detergent, a possible remedy is to trap the protein in the well and wash away the interfering detergent. This approach is used in Examples 2 and 3 below. With the assay procedures described in Examples 1 and 4, serious interference will cause all the wells in the column of protein standards to show the same dye response (usually the maximum absorbance change) rather than the normal, protein concentration-dependent response gradient. This effect can be immediately detected by visual inspection, alerting the user to the problem. Often such interference can be prevented or minimized in subsequent assays by pre-diluting the solutions to allow a normal, protein-based dye response.

EXAMPLE 1

Indicator dye solution was prepared by first dissolving 50 mg of COOMASSIE® Blue G (C.I. #42655) in 25 ml of ethanol (methanol can also be used). The solution was treated with 100 mg of NORIT® and filtered through a glass-fiber filter. The filtered solution was then added to 50 ml of 85% $H_3PO_4$, and diluted to 100 ml with water.

Using an 8-channel syringe dispenser, 20 µl of the resultant indicator dye solution was added to the bottom of each well of a 96-well multiwell plate. Usually several plates (10–20) are prepared at one time. When dry, each well contains 10 µg of COOMASSIE® Blue G and 8.5 mg of $H_3PO_4$. Several ratios of dye, acid and water were evaluated, and this composition gave the best overall response with 250 µl of protein solution.

The multiwell plates were then dried by heating to 70° C. in a vacuum desiccator oven for 5–6 hours, then transferred from the oven to a desiccator, sealed, and cooled to room temperature. Above 70° C., the polystyrene multiwell plate may warp. The length of drying is not critical; 4 hours is adequate for removing the water with reasonable vacuum (less than 1 mm Hg) and a desiccant present. Longer drying tends to make the residue more viscous, probably due to pyro- and poly- phosphate formation. This does not interfere with the assay, and may even decrease hydrolysis due to accidental exposure to atmospheric moisture by acting as an internal desiccant.

After cooling, 5 µl of anhydrous glycerol containing 1M glucose was added to each well using an 8-channel syringe dispenser. The glycerol solution was at room temperature to aid in pipetting. While glycerol alone is quite effective, the added glucose makes it more viscous which allows the plates to be tipped, or even inverted for several hours, without the reagents flowing to the top of the well.

Bovine serum albumin (BSA) standard protein solutions were prepared by dissolving the appropriate amount of BSA in distilled water to produce BSA solutions having the concentrations of BSA shown in Table 1.1. 10 µl aliquots of the BSA solutions were placed into the wells in rows A–H of columns 1,4, 7 and 10 of a multiwell plate like that represented in FIG. 1.1, as described in Table 1.1. (The Bradford assay has been shown to give slightly different slopes for the standard curves of various proteins. For BSA, the response is somewhat greater than average. In general, to estimate the concentration of an "average" protein, the sample protein concentration determined from a BSA standard curve should be multiplied by 0.9. For maximum accuracy with a known protein, the ratio of the standard curves for that protein and BSA should be determined.) The plates were then returned to the desiccator and dried under vacuum for 16 hours at room temperature.

The dried plates were sealed with PARAFILM® or with transparent adhesive tape, with one column of standards and two assay columns under each tape strip. (3M® "Bookbinding" transparent tape is the most convenient tape tested, due to its thickness and strength, but MANCO® "Carton Sealing Tape, CS-55 Clear" also works satisfactorily. It is preferred that the tape and adhesive be hydrophobic to avoid loss of solution to the tape.)

Protein assays were performed by peeling back one tape strip to open three columns of wells, one containing protein standards and two columns of assay wells. An exact volume (250 µl) of the appropriate buffer solution was added to each well in the column of protein standards, and the same buffer solution, but containing protein, was added to the wells of one of the assay columns. Table 1.1 shows the final protein concentration in each of the wells. (Sample volumes of 150 µl to 300 µl per well will give a good response. Of course, the same volume must be added to the wells in the column of standards and the wells in the assay columns.)

For simple visual protein determinations, the same volume (250 µl) of the sample was added to all the wells of a remaining column. (By adding the sample to be determined to all the wells in a column, a simple side-by-side color comparison can be made between the wells in the standard column and the wells in the sample column.) The wells were carefully resealed with the tape strip and the solutions mixed by inverting.

The plate can be read immediately, but the protein-dependent dye response is quite stable, and can still be measured the following day. Using a multiwell plate reader, the absorbance can be read at wavelengths from 590 nm to 630 nm, with the absorbance maximum for the protein-dye complex at about 600 nm. (The tape strip should be carefully peeled back before reading the plate, to avoid the high background absorbance it causes.) Table 1.1 shows the absorbance at 630 nm for the BSA concentrations shown in the table. (The absorbance readings of 8 replicate protein standards had a standard deviation of 0.0055, corresponding to an error range of roughly +/−0.1 µg/ml.) As shown in Table 1.2, for visual protein determinations, the sample concentration is estimated by matching its color to the protein standard with the closest color match. [Visual determinations can be made at protein concentrations from 0–20 µg/ml, with error ranges as shown in Table 1.2.]

TABLE 1.1

COOMASSIE® Blue G-based Protein Assay
Concentration and Absorbance of Incorporated Protein Standards

| Row | Added BSA Conc.* (µg/ml) | Total BSA Added (µg) | Final BSA Conc.** (µg/ml) | Absorbance*** Incorp. Standards[1] | Added Protein[2] |
|---|---|---|---|---|---|
| A | 0 | 0.0 | 0.0 | 0.00 | −0.004 |
| B | 20 | 0.2 | 0.8 | 0.027 | 0.022 |
| C | 50 | 0.5 | 2.0 | 0.088 | 0.065 |
| D | 100 | 1.0 | 4.0 | 0.146 | 0.136 |
| E | 200 | 2.0 | 8.0 | 0.262 | 0.270 |
| F | 500 | 5.0 | 20.0 | 0.414 | 0.411 |
| G | 1000 | 10.0 | 40.0 | 0.511 | 0.512 |
| H | 2000 | 20.0 | 80.0 | 0.562 | 0.560 |
| (Alt. H | 5000 | 50.0 | 200.0 | 0.600 | 0.615) |

*Concentration of the 10 µl BSA solution added to the well.
**Not adjusted for the volume of dye, acid and glycerol; i.e. equivalent to the BSA concentration in 250 µl of buffer.
***Absorbance readings were made using a DYNATECH® MR 580 multiwell plate reader with a 630 nm filter. Zero absorbance was set using the standard well without BSA.
[1]Incorporated anhydrous protein standards.
[2]Protein (BSA) added at the time of the assay, to give the same final concentrations as the standards.

TABLE 1.2

COOMASSIE® Blue G-based Protein Assay
Visual Estimation of Protein Concentration

| Row | BSA Conc.* (µg/ml) | Approx. Visual Detm. Ranges (µg/ml) | Absorbance at 630 nm** |
|---|---|---|---|
| A | 0.0 | 0–0.4 | 0.00 |
| B | 0.8 | 0.4–1.5 | 0.027 |
| C | 2.0 | 1.5–3 | 0.088 |
| D | 4.0 | 3–6 | 0.146 |
| E | 8.0 | 6–12 | 0.262 |
| F | 20.0 | 12–30 | 0.414 |
| G | 40.0 | *** | 0.511 |
| H | 80.0 | *** | 0.562 |
| (Alt. H | 200.0 | *** | 0.600) |

*Not adjusted for the volume of dye, acid and glycerol; i.e. equivalent to the BSA concentration in 250 µl of buffer.
**Absorbance readings were made as in Table 1.1.
***Visual estimations are difficult at these concentrations.

EXAMPLE 2

Nitrocellulose disks, 7 mm in diameter, were prepared from nitrocellulose sheet (0.45 µm pore size, Scheleicher & Schuell, Keene, NH) using a paper punch, and one disk was placed in the bottom of each well of a 96-well multiwell plate. The assay reagent, a solution of copper phthalocyanine 3,4',4",4'''tetrasulfonic acid tetrasodium (CPTS) was prepared by dissolving 50 mg of CPTS (C.I. #42660) in 100 ml of 12 mM HCl.

Using a micropipet, 10 µl of the assay reagent was applied to the nitrocellulose at the bottom of each well of the multiwell plate. Usually several plates (10–20) are prepared at one time. The plates were then dried by heating to 35° C. in a vacuum desiccator oven for 1–2 hours, then transferred from the oven to a desiccator and sealed. The wells in rows A–H of columns 1,4,7 and 10 on each plate were treated with 5 µl of one of the BSA solutions shown in Table 2.1. The plates were returned to the desiccator, and dried under vacuum for 16 hours at room temperature. In this embodiment of the invention, the protein adheres to the nitrocellulose, keeping the protein in the wells during subsequent washing steps.

The dried plates were sealed with transparent adhesive tape, with one column of standards and two assay columns under each tape strip, as in Example 1. Protein assays were performed by peeling back one tape strip to open a column of wells. containing protein standards and two columns of assay wells containing only CPTS. An exact volume (between 2 to 10 µl) of the same buffer solution as that containing the protein to be assayed was added to each well in the column of protein standards.

The same volume of each sample solution having an unknown concentration of protein was added to one or more assay wells for protein determination using a plate reader, or to all the wells of a remaining column for visual determination. After the sample solutions had been added, the wells were washed twice with 250 µl of 12 mM HCl and the liquid removed by aspiration. The washing steps removed unbound dye and most components of the sample solution other than protein. At this point the only CPTS retained in the well was bound to protein, and hence proportional to the amount of protein present.

To determine the amount of dye remaining in the well, the nitrocellulose was made transparent by adding 200 µl of dimethyl sulfoxide to each well. The absorbance at 630 nm was determined using a DYNATECH® Model MR 580 multiwell plate reader. The absorbance at 630 nm reflects the amount of dye bound to the protein in the well and is thus directly proportional to the amount of protein added. Table 2.1 shows the absorbance difference at 630 nm for the BSA concentrations shown in the table.

TABLE 2.1

| | CPTS-based Multiwell Protein Assay | | | |
|---|---|---|---|---|
| Row | Added BSA Conc.* (µg/ml) | Total BSA Added (µg) | Final BSA Conc.** (µg/ml) | Absorbance*** |
| A | 0 | 0.00 | 0.00 | 0.00 |
| B | 10 | 0.05 | 0.25 | 0.010 |
| C | 50 | 0.25 | 1.25 | 0.018 |
| D | 100 | 0.50 | 2.50 | 0.026 |
| E | 200 | 1.00 | 5.00 | 0.050 |
| F | 300 | 1.50 | 7.50 | 0.089 |
| G | 400 | 2.00 | 10.00 | 0.110 |
| H | 0 | 0.00 | 0.00 | 0.00 |

*Concentration of the 5 µl BSA solution added to the well.
**Equivalent to the BSA concentration in 200 µl of buffer.
***Absorbance readings were made using a Dynatech MR 580 multiwell plate reader with a 630 nm filter. Zero absorbance was set using the standard well without BSA.

EXAMPLE 3

A solution of CPTS was prepared by first dissolving 50 mg of CPTS (C.I. #42660) in 100 ml of 200 mM phosphoric acid. Using a micropipet, 40 µl of the dye solution was applied to the bottom of each well of a number of multiwell plates similar to the one shown in FIG. 1.

The plates were then dried by heating to 35° C. in a vacuum desiccator oven for 1–2 hours, then transferred from the oven to a desiccator and sealed. The wells in rows A–H of columns 1, 4, 7 and 10 on each plate were each treated with 5 µl of one of the BSA solutions shown in Table 3.1. The plates were returned to the desiccator, and dried under vacuum for 16 hours at room temperature. The dried plates were sealed with transparent adhesive tape (as in Example 1) with one column of standards and two assay columns under each tape strip.

Protein assays were performed by peeling back one tape strip to open a column of wells containing protein standards and two columns of assay wells. An exact volume (between 2 and 10 µ) of the same buffer solution (except without protein) as the unknown solution whose protein concentration is to be determined was added to each well in the column of protein standards. The same volume of a protein-containing solution was added to one or more assay wells (for protein determination using a plate reader) or to all the wells of a remaining column (for simple visual determination), and the plate was dried.

After the sample solutions have been added and dried, unbound dye was removed by washing each well twice with 250 µl of 12 mM HCl, and the solutions removed by aspiration. The precipitated protein-dye complexes remain bound to the walls of the well. To dissolve the protein-dye complex, 200 µl of 200 mM sodium bicarbonate solution, pH 9.0, was added to each of the washed wells. The plates were read immediately, using a DYNATECH® MR 580 multiwell plate reader. Table 3.1 below shows the absorbance at 630 nm for each of the protein standards.

TABLE 3.1

| | CPTS-based Multiwell Protein Assay | | | |
|---|---|---|---|---|
| Row | Added BSA Conc.* (µg/ml) | Total BSA Added (µg) | Final BSA Conc.** (µg/ml) | Absorbance*** |
| A | 0 | 0.00 | 0.00 | 0.00 |
| B | 10 | 0.05 | 0.25 | 0.004 |
| C | 25 | 0.125 | 0.625 | 0.009 |
| D | 50 | 0.25 | 1.25 | 0.021 |
| E | 100 | 0.50 | 2.50 | 0.037 |
| F | 200 | 1.00 | 5.00 | 0.076 |
| G | 300 | 1.50 | 7.50 | 0.114 |
| H | 400 | 2.00 | 10.00 | 0.170 |

*Concentration of the 5 µl BSA solution added to the well.
**Equivalent to the BSA concentration in 200 µl of buffer.
***Absorbance readings were made using a DYNATECH® MR 580 multiwell plate reader with a 630 nm filter. Zero absorbance was set using the standard well without BSA.

EXAMPLE 4

Indicator dye solution was prepared by first dissolving 100 mg of SERVA® Blue W (C.I. #42645) in 25 ml of ethanol (methanol can also be used). The solution was added to 25 ml of acetic acid and diluted to 150 ml with distilled water. A solution of potassium acetate (9.9M) was added to give a final volume of 200 ml.

Using an 8-channel syringe dispenser, 20 µl of the resultant dye solution was added to the bottom of each well of a 96-well multiwell plate. When dry, each well contains 10 µg of SERVA® Blue W, 4.8 mg of potassium acetate and 2.6 mg of acetic acid. Upon dilution, this gives a final pH of 4.2–4.5. Several other combinations of acid/base buffer components giving this pH range were evaluated and found to to be equally effective with 250 µl of protein solution.

The multiwell plates were then dried at room temperature in a vacuum desiccator for 15–16 hours and sealed. Anhydrous glycerol (5 µl) containing 1M glucose was added to each well using an 8-channel syringe dispenser. The glycerol solution was at room temperature to aid in pipetting.

Bovine serum albumin (BSA) standard protein solutions were prepared by dissolving the appropriate amount of BSA in distilled water to produce BSA solutions having the concentrations of BSA shown in Table 4.1. Aliquots of the BSA solutions were placed into the wells in rows A–H of columns 1,4, 7 and 10 of the multiwell plate, as in Example 1. The plates were then returned to the desiccator and dried under vacuum for 16 hours at room temperature, and the dried plates were sealed as in Example 1.

Protein assays were performed as in Example 1. An exact volume (250 µl) of the appropriate buffer solution was added to each well in the column of protein standards. Table 4.1 shows the final protein concentration in each of the standards.

The same volume (250 µl) of each sample for protein determination was added to one or more assay wells for protein determination using a plate reader, or to all the wells of a remaining column for simple visual determination. (By adding the sample to be determined to all the wells in a column, a simple side-by-side color comparison can be made between the wells in the standard column and the wells in the sample column.) The wells were carefully resealed with the tape strip and the solutions mixed by inverting.

The plates could be read immediately. The wells without protein were bright green, shifting to dark purple with increasing protein concentrations. When using a multiwell plate reader, the absorbance can be read at wavelengths from 590 nm to 640 nm, with the absorbance maximum for the protein-dye complex at about 620 nm. (The tape strip should be carefully peeled back before reading the plate, to avoid the high background absorbance it causes.) Table 4.1 shows the absorbance at 630 nm for the BSA concentrations shown in the table.

TABLE 4.1

SERVA ® Blue W-based Protein Assay
Concentration and Absorbance of Incorporated Protein Standards

| Row | Added BSA Conc.* (µg/ml) | Total BSA Added (µg) | Final BSA Conc.** (µg/ml) | Absorbance*** Incorp. Standards |
|---|---|---|---|---|
| A | 0 | 0.0 | 0.0 | 0.220 |
| B | 20 | 0.2 | 0.8 | 0.238 |
| C | 50 | 0.5 | 2.0 | 0.251 |
| D | 100 | 1.0 | 4.0 | 0.319 |
| E | 200 | 2.0 | 8.0 | 0.394 |
| F | 500 | 5.0 | 20.0 | 0.496 |
| G | 1000 | 10.0 | 40.0 | 0.581 |
| H | 2000 | 20.0 | 80.0 | 0.604 |

*Concentration of the 10 µl BSA solution added to the well.
**Not adjusted for the volume of dye, acid and glycerol; i.e. equivalent to the BSA concentration in 250 µl of buffer.
***Absorbance readings were made using a DYNATECH ® MR 580 multiwell plate reader with a 630 nm filter. Zero absorbance was set using a well without dye or BSA.

Some of the advantages of the solventless protein assay standard of the present invention with particular reference to the Bradford-style assay are listed below.

1. The protein standards can be prepared easily, accurately, and well in advance.

2. Errors due to mislabelled or incorrectly identified protein standard solutions are eliminated.

3. Protein standards having exactly the same nonprotein composition as the samples to be assayed are easily prepared, simply by using the same buffer.

4. Degradation of protein standards by hydrolysis, proteolysis, or bacterial or fungal contamination is prevented by the anhydrous storage conditions.

5. Several protein determinations can be made at the same time, and relative protein concentrations can be determined visually.

6. Common assay errors due to interfering substances in the solutions are immediately obvious by their visible effect on the color changes of the protein standards. Similarly, high sample protein concentrations are quickly obvious, and more dilute samples can be prepared and assayed immediately.

7. Reproducibility is improved because the protein standards and sample assay conditions are more uniform from assay to assay.

8. Sample protein concentrations can be rapidly and easily quantified by visually matching the color of the sample to that of the closest protein standard. More exact quantification also can be made rapidly, using a multiwell plate reader.

9. Only one precise volumetric measurement is required for each standard and sample, the volume of solution added to the well. This volume, at around 250 µl, can be measured conveniently and accurately.

10. Additional samples may be assayed using the same protein standards, as long as they are in the same buffer and are appliDed soon after the standards.

11. The solventless assay media are more stable than the stock assay solutions, and do not require filtering or mixing immediately prior to use.

12. The unused, sealed plates can be stored at room temperature, and are more compact and easily stored than other assay components and standards.

13. The resealed plates are quite stable, and can usually be analyzed several days after preparation with little loss in sensitivity or accuracy.

14. The measurable protein concentration range, over 3 orders of magnitude, is greater than the standard Bradford assay.

15. The sensitivity is increased because the sample is not diluted in assay buffer.

What is claimed is:

1. A method for preparing a solventless protein standard comprising the steps of:

preparing a dye solution containing a dye and dye solvent;

placing an aliquot of the dye solution within a receptacle;

removing the dye solvent from the receptacle;

preparing a protein solution containing a known amount of protein and a known amount of protein solvent;

placing a known amount of the protein solution within the receptacle containing the dye without the dye solvent such that the amount of protein within the receptacle can be calculated wherein the dye does not substantially solubilize upon the placing of said protein solution; and removing the protein solvent from the receptacle under conditions to prevent hydrolysis of the protein.

2. The method as recited in claim 1, wherein a protectant is placed in between the dye and the protein.

3. The method as recited in claim 2, wherein the protectant is selected from the group consisting of anhydrous glycerol and glucose.

4. The method as recited in claim 1 wherein the protein is Bovine Serum Albumin.

5. A solventless protein standard produced according to the method of claim 1.

6. A method for preparing a solventless protein standard comprising the steps of:

preparing a protein solution containing a known amount of protein and a known amount of protein solvent;

placing a known amount of the protein solution within a receptacle such that the amount of protein within the receptacle can be calculated;

removing the protein solvent from the receptacle;

preparing a dye solution containing a dye and dye solvent;

placing an aliquot of the dye solution within the receptacle containing the protein without the protein solvent, wherein the protein does not substantially solubilize upon the placing of said dye solution; and removing the dye solvent from the receptacle under conditions to prevent hydrolysis of the protein.

7. The method as recited in claim 6, wherein a protectant is placed in between the dye and the protein.

8. The method as recited in claim 7, wherein the protectant is selected from the group consisting of anhydrous glycerol and glucose.

9. The method as recited in claim 6 wherein the protein is Bovine Serum Albumin.

10. A method for determining the total concentration of total protein in a solution comprising the steps of:

preparing a dye solution containing a dye and dye solvent;

placing an aliquot of the dye solution into each of a series of separate receptacles;

removing the dye solvent from the separate receptacle;

preparing a number of separate protein solutions, each protein solution containing a different known amount of protein and a known amount of protein solvent wherein the concentration of protein within each solution is known and is different than the concentration of the other solutions;

placing a known amount of each of the protein solutions into the separate dye containing receptacles such that the amount of protein within each receptacle is different;

removing the protein solvent from the separate receptacles;

placing an aliquot of the dye solution in a receptacle which does not contain protein;

removing the dye solvent from the receptacle which does not contain protein so as to produce a receptacle which contains dye but does not contain protein;

adding a predetermined uniform volume of solvent to each of the separate receptacles which contain protein so as to produce detectable visual protein-dye reaction wherein the visual protein dye reaction in each of the separate receptacles has an intensity which corresponds to the concentration of protein within each of the separate receptacles;

adding a volume of an unknown protein solution to the receptacle containing dye without protein, the volume of unknown protein solution being in an amount equal to the volume of solvent added to the protein-dye containing receptacles, wherein the protein in the unknown solution reacts with the dye to produce a detectable visual protein-dye reaction which has a measurable intensity; and comparing the intensity of the protein-dye reaction within the receptacle containing the unknown protein solution with the intensities of the protein-dye reactions of the receptacles containing known amounts of protein so as to determine the concentration of protein within the unknown protein solution.

11. A method for determining the total concentration of total protein in a solution comprising the steps of:

preparing a number of separate protein solutions, each protein solution containing a different known amount of protein and a known amount of protein solvent wherein the concentration of protein within each solution is known and is different than the concentration of the other solutions;

placing a known amount of each of the separate protein solutions into separate receptacles such that the amount of protein within each receptacle is different;

removing the protein solvent from the separate receptacles;

preparing a dye solution containing a dye and dye solvent;

placing an aliquot of the dye solution into each of the protein-containing receptacles;

removing the dye solvent from the protein containing receptacle;

placing an aliquot of the dye solution in a receptacle which does not contain protein;

removing the dye solvent from the receptacle which does not contain protein so as to produce a dye-containing receptacle which contains dye but does not contain protein;

adding a predetermined uniform volume of solvent to each of the receptacles which contain protein and dye so as to produce a detectable visual protein-dye reaction wherein the visual protein-dye reaction in each of the protein containing receptacles has a measurable intensity which corresponds to the concentration of protein within each of the protein containing receptacles;

adding a volume of an unknown protein solution to the receptacle containing dye without protein, the volume of unknown protein solution being in an amount equal to the volume of solvent added to the protein-dye containing receptacles, wherein the protein in the unknown solution reacts with the dye to produce a detectable visual protein-dye reaction which has a measurable intensity; and comparing the intensity of the protein-dye reaction within the receptacle containing the unknown protein solution with the intensities of the protein-dye reactions of the receptacles containing known amounts of protein so as to determine the concentration of protein within the unknown protein solution.

* * * * *